US009396587B2

(12) United States Patent
Znamenskiy et al.

(10) Patent No.: US 9,396,587 B2
(45) Date of Patent: Jul. 19, 2016

(54) SYSTEM FOR ACCESSING DATA OF A FACE OF A SUBJECT

(71) Applicant: KONINKLIJKE PHILIPS N.V., Eindhoven (NL)

(72) Inventors: Dmitry Nikolayevich Znamenskiy, Eindhoven (NL); Karl Catharina Van Bree, Eindhoven (NL); Octavian Soldea, Kiryat-Bialik (IL); Hong Liu, Eindhoven (NL); Franciscus Hendrikus Van Heesch, Eindhoven (NL); Ruud Vlutters, Eindhoven (NL)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 0 days.

(21) Appl. No.: 14/433,958

(22) PCT Filed: Oct. 1, 2013

(86) PCT No.: PCT/IB2013/059039
§ 371 (c)(1),
(2) Date: Apr. 7, 2015

(87) PCT Pub. No.: WO2014/057392
PCT Pub. Date: Apr. 17, 2014

(65) Prior Publication Data
US 2015/0262422 A1 Sep. 17, 2015

Related U.S. Application Data

(60) Provisional application No. 61/712,897, filed on Oct. 12, 2012.

(51) Int. Cl.
*G06K 9/00* (2006.01)
*G06T 17/20* (2006.01)
(Continued)

(52) U.S. Cl.
CPC ............ *G06T 17/20* (2013.01); *G06K 9/00201* (2013.01); *G06K 9/00228* (2013.01);
(Continued)

(58) Field of Classification Search
USPC ......... 382/100, 103, 106–108, 118, 123, 128, 382/140–141, 154, 168, 173, 181, 193, 199, 382/203, 209, 219, 232, 254, 266, 274–276, 382/285–294, 305, 312, 321, 224; 128/206.21, 205.25, 848, 207.15
See application file for complete search history.

(56) References Cited

U.S. PATENT DOCUMENTS 7,127,081 B1 10/2006 Erdem
7,274,822 B2 * 9/2007 Zhang ............... G06F 17/30265
382/224

(Continued)

FOREIGN PATENT DOCUMENTS

CN 1975323 A 6/2007
GB 2449855 A 12/2008

OTHER PUBLICATIONS

Anonymous: "Fotowand Mona Lisa 94×64 cm gunstig kaufen bei PartyDeko.de", Jun. 23, 2012, XP055090864,Retrieved from the Internet: URL: https://web.archi ve.org/web/20120623112814/ http://www.partydeko.de/fotowand-mona-li sa-94-x-64-cm.html [retrieved on Nov. 29, 2013].

(Continued)

*Primary Examiner* — Seyed Azarian
(74) *Attorney, Agent, or Firm* — Michael W. Haas

(57) ABSTRACT

The present invention relates to a template (10) and a system (50) for collecting data of a face of a subject. The system (50) comprises at least the template (10) and a camera (52). The template (10) comprises at least one computer-detectable element and allows to take a single image of a face of a subject which is positioned in an opening of the template and to derive subject dimensions of the face of the subject based on this single image. The present invention relates also to according methods.

22 Claims, 9 Drawing Sheets

(51) Int. Cl.
*G06T 7/00* (2006.01)
*G06T 7/60* (2006.01)
*G06K 9/20* (2006.01)
*H04N 13/02* (2006.01)
*A62B 18/02* (2006.01)

(52) U.S. Cl.
CPC .......... *G06K9/00268* (2013.01); *G06K 9/2063* (2013.01); *G06T 7/0065* (2013.01); *G06T 7/60* (2013.01); *H04N 13/026* (2013.01); *G06T 2200/08* (2013.01); *G06T 2207/20088* (2013.01); *G06T 2207/30201* (2013.01); *G06T 2207/30208* (2013.01); *G06T 2210/41* (2013.01); *G06T 2215/16* (2013.01)

(56) References Cited

U.S. PATENT DOCUMENTS

| | | | |
|---|---|---|---|
| 2004/0161134 A1 | 8/2004 | Kawato | |
| 2007/0183653 A1 | 8/2007 | Medioni | |
| 2008/0035158 A1* | 2/2008 | Pflueger | A61F 2/00 128/848 |
| 2008/0060652 A1* | 3/2008 | Selvarajan | A61M 16/06 128/206.21 |
| 2008/0078396 A1* | 4/2008 | Janbakhsh | A61M 16/06 128/205.25 |
| 2008/0298643 A1 | 12/2008 | Lawther | |
| 2011/0203594 A1* | 8/2011 | Brain | A61M 16/04 128/207.15 |
| 2014/0056510 A1 | 2/2014 | Van Bree | |
| 2015/0128953 A1* | 5/2015 | Formica | A61M 16/0683 128/206.21 |

OTHER PUBLICATIONS

Mishima K et al: "Production of a Range Image for Facial Motion Analysis: A Method for Analyzing Lip Motion", Computerized Medical Imaging and Graphics, Pergamon Press, New York, NY, US, vol. 30, No. 1, Jan. 1, 2006, pp. 53-59, XP024903623.

Viola et al., "Rapid Object Detection using a Boosted Cascade of Simple Features", Accepted Conference on Computer Vision and Pattern Recognition, 2001, pp. 1-9.

Redert Peter-Andre, "Multi-Viewpoint Systems for 3-D Visual Communication", PhD Thesis, University of Delft, 2000, ISBN 90-901-3985-0.

Vetter Thomas et al., "Estimating Coloured 3D Face Models from Single Images: An Example Based Approach", Max-Planck-Institut für biologische Kybernetik Spemannstr. 38 72076 Tübingen, Germany, H. Burkhardt, B. Neumann (Eds.) Computer Vision—ECCV '98, vol. II, LNCS 1407, pp. 499-513,1998. Springer-Verlag Berlin Heidelberg.

Vlutters R. et al., "3D Mask Sizing: Progress 2010", Koninklijke Philips Electronics N.V. 2011, Philips Technical Note PR-TN 2011. Artkoolkit http://www.hitl.washington.edu/artoolkit/ Aug. 5, 2004 (estimated).

* cited by examiner

SYSTEM FOR ACCESSING DATA OF A FACE OF A SUBJECT

CROSS-REFERENCE TO RELATED APPLICATIONS

This patent application claims the priority benefit under 35 U.S.C. §371 of International Patent Application No. PCT/IB2013/059039, filed Oct. 1, 2013, which claims the priority benefit under 35 U.S.C. §119(e) of U.S. Provisional Application No. 61/712,897 filed on Oct. 12, 2012, the contents of which are herein incorporated by reference.

FIELD OF THE INVENTION

The present invention relates to a template and a system for collecting data of a face of a subject, as well as to a corresponding method for collecting data and a method for collecting 3D-data of a face of a subject.

BACKGROUND OF THE INVENTION

Patient interfaces, such as masks for covering the mouth and/or nose, are used for delivering gas to a subject. Such gases, like air, cleaned air, oxygen, or any modification of the latter, are submitted to the subject via the patient interface in a pressurized or unpressurized way.

For several chronic disorders and diseases, a long-term attachment of such a patient interface to a subject is necessary or at least advisable.

One non-limiting example for such a disease is obstructive sleep apnoea or obstructive sleep apnoea syndrome (OSA). OSA is usually caused by an obstruction of the upper airway. It is characterized by repetitive pauses in breathing during sleep and is usually associated with a reduction in blood oxygen saturation. These pauses in breathing, called apnoeas, typically last 20 to 40 seconds. The obstruction of the upper airway is usually caused by reduced muscle tonus of the body that occurs during sleep. The human airway is composed of walls of soft tissue which can collapse and thereby obstruct breathing during sleep. Tongue tissue moves towards the back of the throat during sleep and thereby blocks the air passages. OSA is therefore commonly accompanied with snoring.

Different invasive and non-invasive treatments for OSA are known. One of the most powerful non-invasive treatments is the usage of Continuous Positive Airway Pressure (CPAP) or Bi-Positive Airway Pressure (BiPAP) in which a patient interface, e.g. a face mask, is attached to a tube and a machine that blows pressurized gas, preferably air, into the patient interface and through the airway in order to keep it open. Positive air pressure is thus provided to a subject through a hose connected to a patient interface or respiratory interface, such as a face mask, that is worn by the subject. The afore-mentioned long-term use of the patient interface is the result, since the wearing of the patient interface takes place during the sleeping time of the subject.

Examples for patient interfaces are:
nasal masks, which fit over the nose and deliver gas through the nasal passages,
oral masks, which fit over the mouth and deliver gas through the mouth,
full face masks, which fit over both, the nose and the mouth, and deliver gas to both, total face masks, which fit over the whole face, and
nasal pillows, which are regarded as masks as well within the scope of the present invention and which consist of small nasal inserts that deliver the gas directly to the nasal passages.

The patient interface is usually positioned on the subject's head using some kind of headgear. Wearing a patient interface can be uncomfortable, since for providing an airtight seal between the patient interface and the subject's face, the patient interface has to be worn tightly on the face.

If the patient interface does not fit well on the subject's face, the wearing of the patient interface can be even more uncomfortable. Further, such a "wrong" patient interface for the respective subject results easily in pressure points and red marks once the patient interface is removed, which is undesired. Furthermore, such a patient interface applied to a subject might suffer from several gas leaks in the contact zone to the subject's face, making the whole treatment inefficient or even ineffective.

In order to reduce these disadvantages, i.e. the wearing being uncomfortable, resulting in the formation of red marks and leading to inefficient treatments, patient interfaces are provided in different sizes and forms such that there is preferably for every subject a suitable patient interface. In order to find a fitting patient interface for an individual subject, a search within a pool of different patient interfaces can be done based on trial and error or by measuring the face of the subject.

Both methods, i.e. trial and error as well as an exact measurement of the face proportions according to known methods, are very time consuming and provide also a lot of error sources. While in the trial and error method the choice basically depends on the subject evaluating the fit of the mask by himself/herself which can deviate from the objective fitting quality, detailed measurements in the face of the subject in order to determine several distances and proportions can be erroneous and may also be subject to error accumulation. Further, when using image recording equipment for the measurement an additional means to retrieve scale needs to be disposed in the background.

SUMMARY OF THE INVENTION

It is an object of the present invention to provide a system and a method that assists in selecting and allows an optimal choice of a patient interface for an individual subject such that the patient interface fits comfortable on the subject's face.

According to an aspect of the present invention, a template for collecting data of a face of a subject is provided, with
a surface,
an opening for the face of the subject in the surface, and
at least one marking on the surface that is detectable by a computer for providing dimensional reference information.

Preferably, the collection of data of a face of the subject is a collection of anthropometric data of a face of a subject.

According to another aspect of the present invention, a system for collecting data of a face of a subject is provided, with
a template for collecting data of a face of a subject, having
a surface, an opening for the face of the subject in the surface and at least one computer-detectable element for providing dimensional reference information, and
a camera for recording image data of the template and the face of the subject within the opening of the template, preferably wherein the template is a template according to the present invention.

The term "dimension" as used within the context of the present invention is to be understood as encompassing dimensions such as but not limiting to lengths, widths and angles.

The term "computer-detectable element" as used within the context of the present invention is to be understood as any structural element on the respective template that may provide dimensional reference information in an image of the template and that can be derived by a computer, either by known dimensions of the computer-detectable element itself or by known dimensions based on the distance between at least two computer-detectable elements. Such a computer-detectable element may therefore be any basic structural element of the template itself, having a defined position, like, but not limiting to the corners of the template. Also, any suitable element provided on the template, like a marking on the surface can be used. The surface here includes the internal and/or external boundaries of the template. A preferred embodiment of a computer-detectable element is a marking according to the present invention.

The term "marking" as used within the context of the present invention is to be understood as an element that is provided on the template, i.e. its surface, and is detectable for a computer due to its suitable contrast, and further comprises a defined position and/or defined dimensions. Based on these, a computer may than be able to derive dimensional reference information in an image, either by the known dimensions of the marking or by known dimensions based on the distance between at least two markings. The marking can be realized by structural modifications in the surface, including the internal and/or the external boundaries, of the template, like cut-outs. Preferably the marking is realized by an imprint, either directly on the surface or via a label, e.g. an adhesive label.

The term "anthropometric" as used within the context of the present invention is to be understood as encompassing especially the absolute and relative sizes and distances of and between the individual face features and facial landmarks in the face of a subject, like but not limiting to the length and width of the nose, distance from chin to upper nose end, distance between the cheeks, widths of the mouth etc. Further, these data also include the respective positions of the face features and facial landmarks themselves which can be used for computing the mentioned distances and sizes.

The term "detectable by a computer" as used within the context of the present invention is to be understood as not being limited to the usage of a computer per se but referring to the ability of computers and computer-like devices, like but not limiting to smartphones, tablet PCs, digital cameras etc., to detect and recognize the respective marking in image data.

The term "camera" as used within the context of the present invention is to be understood as any suitable camera that is able to generate image data of an object. This image data can either be 2D image data or 3D image data. Exemplary cameras within the context of the present invention are a digital camera, a web camera, an integrated camera in a computer, a camera in a tablet PC or a smartphone, for example.

Such a template is a very easy to use object that assists in the collection of data, preferably anthropometric data of a face of a subject in the combination with a device for recording images, like a digital camera. Therein, the opening is preferably equipped with such a size and shape such that the face of the subject fits within this opening in a way that the relevant face features, like nose, mouth, chin, cheeks or eyes can be seen and detected whereas the remaining part of the head is covered by the surrounding surface around the opening. This provides a clear background, especially when a defined color, like for example white, blue, red, green etc., is used for the surface. Thereby, a defined segmentation between the face and the background is possible without the necessity of computing intensive and time consuming algorithms. Accordingly, the face can easily be localized on an image. Further, by the at least one marking a reference is provided in the image. Therefore, this at least one marking comprises preferably known characteristics, like for example height, width, pattern etc. Furthermore, due to the afore mentioned opening that fits to the face of the subject the most important facial dimensions of the afore mentioned face features, such as but not limiting to nose width and height, mouth width and the facial height are located approximately in the same plane as the template. Therefore, the facial dimensions of the subject, meaning the desired data of the face of the subject can preferably be derived from comparing the respective positions and distances in a 2D representation of the face and the template, e.g. in an image, with known data of the at least one marking, like width, height or distances between several markings.

According to an embodiment of the template, the template comprises several markings. Several markings provide the possibility of including further reference data in the template, i.e. the distances between those several markings. Further, the plurality of markings can be designed such that each marking has a different design, shape or pattern. Those different properties can be used in order to reduce errors that may occur when the respective marking is detected on the image by a computer or computer-like device and the reference data, which is accordingly used to determine the subject dimensions of the face, is derived from just one marking. By using several markings this error can be basically eliminated by averaging above all the determined reference data. In order to also reduce the risk of errors due to a partly inaccurate optics system of a camera or the like, the several markings can be evenly distributed over the whole template in a preferred embodiment.

According to another embodiment of the template, the template is manufactured of a sheet-like material, and in a further preferred embodiment, the template is made of a sheet of paper. Providing the templates by a sheet-like material results in an easy to handle template that is light weight and can be easily transported. Especially by using paper, a material is used that is easily available, relatively cheap and also thin and light weight.

According to another aspect of the present invention, a method for providing a template according to the present invention with the following steps is provided:

printing at least one marking and at least one cut marking for an opening on a printable sheet, and cutting out the opening based on the at least one cut marking. This way, the template can be easily manufactured and a template is provided that can also be easily distributed to users, even in a way such that they can complete the manufacturing of the template. This can be realized by sending the respective sheet to the users in a ready to use form, or without the last step of cutting out the opening completed such that the structural integrity of the sheet material is not reduced during a shipment, for example. The user may then carry out this last step by himself/herself. Further, especially if a sheet of paper is used for the template, the template may be provided to a user in an electronic way, like via electronic mail or via download from the internet, for example. The user can then download the template in a file format that preferably is an appropriate graphical file format that preserves absolute dimensions so that the template dimensions are kept absolute. An example for such a format is the commonly known PDF-format. A user can then print this template and finish the manufacturing process by the last step of cutting out the opening. Thereby, an easy distribution of the template is possible and a user may easily make use of the template according to the present invention.

The term "user" as used within the present invention is to be understood as referring to any user of the devices and methods according to the present invention. This can for example be a manufacturer or provider of the patient interfaces. Alternatively "user" may also refer to (medical) professionals or a subject. These two would especially benefit from the easy way of providing the template as mentioned before. A subject could make use of the afore mentioned template by printing it out at home and sending images of himself/herself to a professional or provider/manufacturer of the patient interfaces, for example.

According to another aspect of the present invention, a computing device is provided, configured to provide subject facial dimensions of a subject based on image data of the face of the subject and at least one computer-detectable element, the computing device comprising:
- at least one output interface, for providing the subject facial dimensions,
- at least one input interface, for receiving the image data of the face of the subject and the at least one computer-detectable element,
- a processing unit including a processor and a memory, the memory storing one or more routines executable by the processor, the one or more routines being adapted to:
- process the image date, and to
- provide subject dimensional data of the face of the subject based on the image data.

The term "subject dimensional data" as used within the context of the present invention is to be understood as referring to the dimensional data, e.g. dimensions, positions, sizes etc., on a real object, e.g. a subject's face or also the template, in contrast to the corresponding data that can be directly derived from an image without any reference or processing, which could be regarded as image dimensional data.

The computing device is able to beneficially carry out the steps for providing the subject dimensional data of the subject's face as mentioned before via the processing unit. Thereby, the processing unit may in the end provide the data, preferably the anthropometric data of the face of the subject based on the image data recorded by, for example, a camera. For this, the computing device recognizes the at least one computer-detectable element on the surface of a template, for example, and is able to derive the reference data of the at least one computer-detectable element, preferably the markings of a template. Further, the computing device is preferably able to recognize the face features or facial landmarks of the face of the subject in order to determine the afore mentioned facial dimensions and can then transform the data achieved this way by using the reference data determined based on the at least one computer-detectable element. Alternatively or additionally the computing device may accept a user input regarding the location of the face features and/or facial landmarks in the image data, for example in the case where an automatic detection by the processing unit fails or is inaccurate. As a result, the subject dimensions of the face and its features can be provided.

The term "computing device" as used within the present invention is to be understood as any suitable device that may carry out the mentioned operations. Preferred embodiments for such a computing device are a personal computer or a portable electronic device, such as but not limiting to a mobile phone, like a smartphone, tablet PC, digital camera etc. In such an embodiment, "the at least one output interface" may be any device suitable for communication with a user, like but not limiting to a display. Accordingly, "the at least one input interface" can be either regarded as any connection to an image recording device, like a camera or the like, or also as the image recording device, e.g. the camera, itself.

Considering an embodiment with distant or cloud computing, "computing device" may also be any distant computer or server that shows the features according to the present invention. Therein, "the at least one output interface" and "the at least one input interface" are for example realized by virtual interfaces, like ports of a server etc. Further, those interfaces can also be regarded as the local device that is or may get in contact with the distant computing device, e.g. via the internet, and therefore acts as the interfaces between this distant computing device and the user.

According to another embodiment of the computing device, the one or more routines are further adapted to:
- generate 3D data from several 2D images by using the at least one computer-detectable element as common reference in the images. Such a design of a computing device allows further to not only determine the subject dimensions of a face of a subject in order to find or design a patient interface, like a face mask, that fits to the subject in an optimal way, but also provides the possibility of generating a 3D model of the face. Thereby, an exact model of a patient interface can be realized or may at least be tested via a computer system. By generating this 3D data out of several 2D images with the aid of the computer-detectable element in a template, for example, it is possible that a user may capture the relevant 2D images with a digital camera or a smartphone, for example, and either let the respective device generate the 3D data or send the 2D images to the provider of the patient interface equipment in order to find the most suitable mask for the subject. If the subject is the user, again an easy way of creating and providing the respective 3D data can be achieved if he/she uses his/her own digital camera or smartphone, for example.

According to another embodiment of the computing device, the one or more routines are for the generation of 3D data further adapted to:
- receive several 2D images of the face of the subject and the at least one computer-detectable element from different positions,
- determine the distance and orientation of the face and the at least one computer-detectable element in the respective images based on the image data of the at least one computer-detectable element, and
- construct 3D data based on the 2D image data and the distance and orientation determined for each image. This embodiment describes an exemplary way how the generation of 3D data by several 2D images may be realized. Therein and in the following analogue aspects and embodiments, the different positions are preferably different orientations.

According to another embodiment of the computing device, the one or more routines are further adapted to:
- determine at least one reference distance based on the at least one computer-detectable element in the image data,
- determine facial dimensions based on facial landmarks in the image data,
- scale the image dimensions in the image data to subject dimensions based on the ratio of the at least one reference distance in the image data to a corresponding known subject reference distance based on the at least one respective computer-detectable element,
- provide the subject facial dimensions, preferably wherein the routines are further adapted to:
- detect the facial landmarks in the image data of the face of the subject.

The term "facial landmarks" as used within the context of the present invention is to be understood as the features or objects in the face of a subject that are relevant to know with respect to their dimensions and positions for providing a patient interface that fits in an optimal way to the subject. Those facial landmarks are for example the nose, the nose wings, the eyes, the mouth, the mouth corners, the cheeks, the chin etc. They therefore may correspond or be identical to the aforementioned face features.

The term "subject (facial) dimensions" as used within the context of the present invention is to be understood as referring to dimensions, like distances, length, height etc., of the real object, e.g. the subject's face or the template, in contrast to the respective dimensions in and determined by the image data directly without any references or processing, which can be regarded as image dimensions. Accordingly, "subject (reference) distance" refers to this special dimension of the real object.

The computing device is able to carry out the method according to the present invention. Therefore, it may receive the image data from a camera, which may be a part of the computing device or the system according to the present invention in a preferred embodiment, via an input interface. Also, it may provide the subject facial dimensions via an output interface, like a display, printer etc, to a user directly, that is to say as raw subject dimensional data. Alternatively, it may also provide processed information in form of an advice which patient interface(s) might be suitable for the subject, for example.

In the preferred embodiment, the computing device may determine the facial landmarks itself and without the data of the facial landmarks being transmitted from another device or being entered by a user. In the more preferred embodiment as mentioned before, the computing device may then work in a completely automatic way, such that it only needs the image data for providing the subject facial dimensions, or already advices on suitable patient interfaces for the subject.

In an alternative embodiment of the computing device, the facial landmarks are provided to the computing device by a user. This may for example be realized via another input interface. Such an input interface may be a keyboard, a computer mouse, a touch screen etc.

In these embodiments as well as in the following methods according to the present invention, the facial landmarks may either be provided by a user input or another system, for example. One example would be an identification of the respective facial landmarks by a user via an interface. Preferably, these facial landmarks are detected by the computing device itself.

According to another embodiment of the computing device, the scaling of the image dimensions in the image data includes perspective corrections. This allows to consider images that are taken from an angle that would lead to distorted data.

According to another embodiment of the computing device, the computing device further comprises a camera. Such a computing device can be designed as a compact device, which can be handled easily. In this embodiment, the camera may directly submit the image data to the at least one input interface.

According to an embodiment of the system, the system further comprises
  a computing device with a processing unit for processing the image data according to the present invention,
  wherein the camera is designed to send the image data to the computing device, and
  wherein the computing device is designed to receive the image data from the camera via the at least one input interface. The set up of this system can be in different advantageous ways, like providing a template and a camera on the user's side whereas the computing device is located at a distant site, for example at the location of the provider or manufacturer of the patient interface, or in general accessible via and/or hosted in the internet, for example.

According to another embodiment of the system, the camera and the computing device are combined in one device. This way, a compact design of the whole system can be achieved by comprising the template and the combined device of the camera and the computing device. Exemplary embodiments of such a combined device can be for example a computer with a web cam, a tablet PC or smartphone with a camera or a digital camera comprising the necessary processing capabilities.

According to another aspect of the present invention, a method for collecting data of a face of a subject is provided, with the following steps
  providing an image of the face of the subject and of at least one marking,
  providing facial landmarks in the image of the face,
  determining at least one reference distance based on the at least one marking in the image,
  determining facial dimensions based on the facial landmarks in the image,
  scaling the image dimensions in the image to subject dimensions using the at least one respective marking, and
  providing the subject facial dimensions, wherein the step of scaling the image dimensions to subject dimensions is preferably based on the ratio of the at least one reference distance in the image to a corresponding known subject reference distance based on the at least one respective marking.

According to another embodiment of the method for collecting data of a face of a subject,
  the image of the face of the subject and of the at least one marking is provided to and received by a computing device, and
  the computing device provides the subject facial dimensions. This way, the method can be and is preferably carried out via a computing device. In a more preferred embodiment, the computing device also performs the remaining steps of the method, like determining the reference distance and the facial dimensions in the image as well as scaling of the image dimensions. In such a preferred embodiment, the facial landmarks may either be provided to the computing device or may be provided, i.e. determined by the computing device itself.

According to another embodiment of the method for collecting data of a face of a subject, the method further comprises at the beginning the steps of
  providing a template according to the present invention, and
  positioning the face of the subject in the opening.

According to another aspect to the present invention, a method for collecting 3D data of a face of a subject is provided, with the following steps
  providing at least two 2D images of the face of the subject and at least one marking from different positions,
  determining the distance and orientation of the face and the at least one marking in the respective images based on the image data of the at least one marking, and
  constructing 3D data based on the 2D image data and the determined distance and orientation for each image. By this method, a very easy collection of 3D data of a subject's face is achieved when the template according to the present invention is preferably used. Due to the known dimensions and pattern of the respective at least one marking, a determination of a distance and orientation of the face in the image, or in other words of the camera that took the image of the face, can be realized such that an easier reconstruction of the 3D data is possible based on several 2D images.

In another embodiment of the method for collecting 3D data, the method comprises further the following steps
providing facial landmarks in the image data of the face,
determining at least one reference distance based on the at least one marking in the image data,
determining facial dimensions based on the facial landmarks in the image data, and
scaling the image dimensions in the image data to subject dimensions based on the ratio of the at least one reference distance in the image data to a corresponding known subject reference distance based on the at least one respective marking. Hereby, "image data" is preferably to be understood as the 3D image data.

According to other aspects of the present inventions, computer programs are provided that comprise program code means for causing a computer to carry out the steps of any one of the afore mentioned methods when said computer program is carried out on a computer. Such computer programs or computer program products may be provided in any suitable way. This can for example be on a storage medium, on a computing device, or via data transfer, like via the Internet or any other suitable way as it will also be described later.

BRIEF DESCRIPTION OF THE DRAWINGS

These and other aspects of the invention will be apparent from and elucidated with reference to the embodiment(s) described hereinafter. In the following drawings

DETAILED DESCRIPTION OF THE INVENTION

Figure 1:
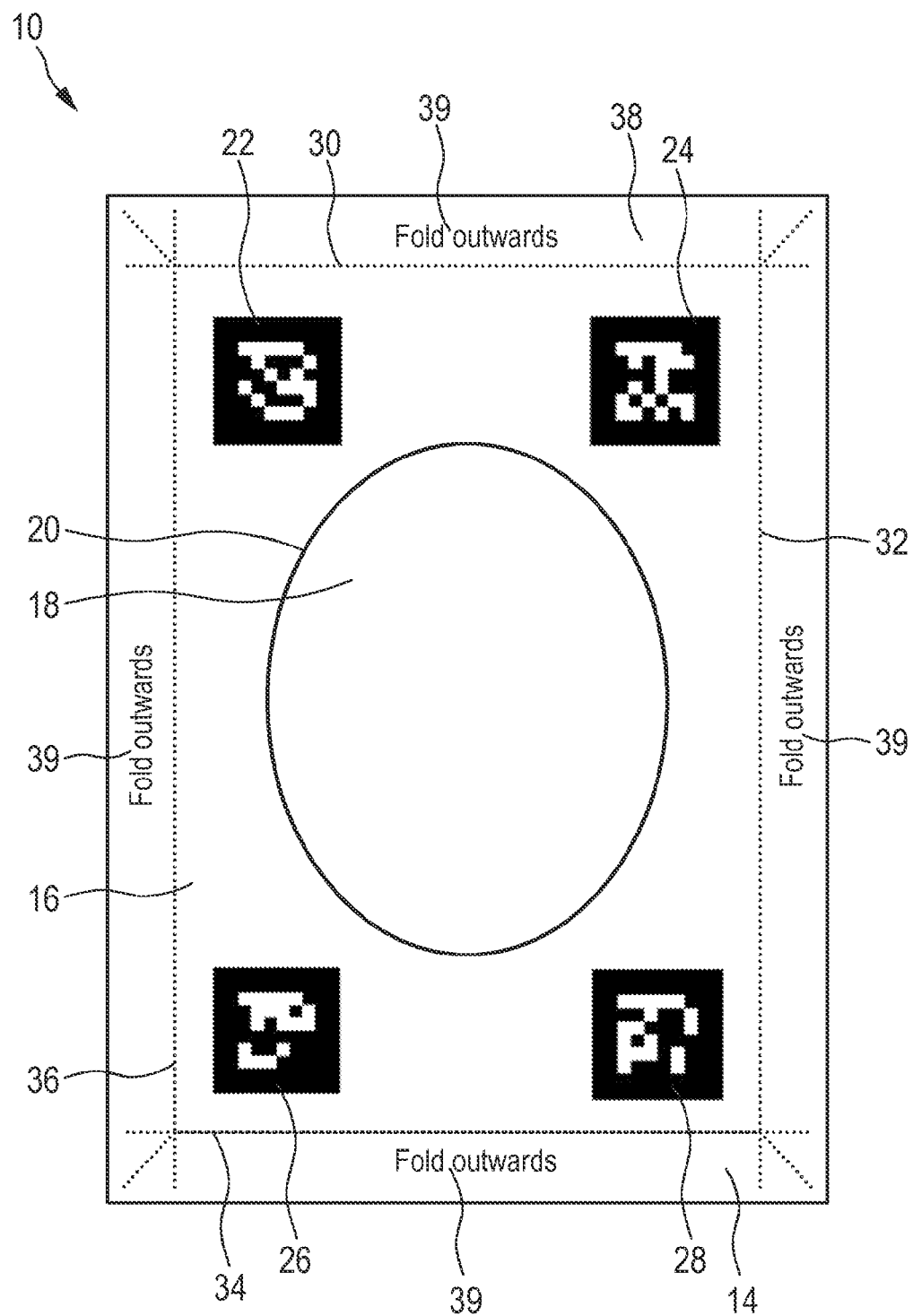
FIG. 1 shows a schematic view of a first template according to an embodiment of the present invention.

Embodiments of a template according to the present invention are shown throughout and described with the help of FIGS. 1 to 10 and are designated in their entirety by the reference numerals 10, 11, 12 and 13, respectively. Further, a system according to the present invention comprising the template 10 is shown throughout and described with the help of FIGS. 5 to 10 and is designated in its entirety by the reference numeral 50.

The template 10 shown in FIG. 1 is manufactured of and therefore comprises a sheet 14 which is in the present embodiment a sheet of paper. The template 10 therefore also comprises a surface 16, which is one side of the sheet 14. In the surface 16 an opening 18 is disposed. This opening 18 is in the present embodiment arranged approximately in the middle of sheet 14. Surrounding opening 18 cut markings 20 can be seen in the present representation of template 10. These cut markings 20 are used in the manufacturing of the template 10 which will be explained later on.

On the sheet 14, markings 22, 24, 26 and 28 are provided. Those four markings 22, 24, 26 and 28 are in this embodiment of template 10 arranged in an evenly distributed manner around the opening 18. Since they form a reference in image data as will be explained, they can be regarded as fiducial markers. A fiducial marker is an object used in the field of view of an imaging system which appears in the image produced, for use as a point of reference or a measure. With four markings as in template 10 each marking is arranged in one edge of the rectangular sheet 14. In template 10 the markings 22, 24, 26 and 28 are in this certain embodiment realized by matrix-code like fiducial markers. Those matrix-code fiducial markers form a reliable marking on the sheet 14 such that a computer or computer-like device can detect those markings 22, 24, 26 and 28 and is on the one hand further able to determine an orientation of the sheet 14 with respect to a camera recording an image and on the other hand able to determine a ratio between the distance in the image taken by a camera and the real or subject distance that corresponds to the distance in the image. In other words, the markings basically allow determining the scale between the image and reality. Therefore, the distances between the markings 22, 24, 26 and/or 28 are respectively known. This means that either the horizontal and vertical distances are known but also that the diagonal distances like distance between marking 24 and marking 26, can be known. Basically, any suitable distance or a combination of distances between the markings 22, 24, 26 and/or 28 should be known in order to use the template according to the present invention. Those distances or dimensions are also referred to as reference subject distance/dimension within the present invention. Another possibility would be that the dimensions of the respective markings 22, 24, 26 and/or 28 are known instead or additionally. This means that by the width and height of one or even each marking the afore mentioned scale can be determined. The information/data derivable from the markings 22, 24, 26 and 28 is further extended by their design. Since due to the matrix-like pattern each marking 22, 24, 26 or 28 is different from the others, each marking can be identified and the derived information can be assigned to the respective location on the template 10, i.e. on surface 16.

Since the sheet 14 is easily bendable, an additional fixation of the sheet 14 is useful in order to prevent any unwanted bending or deformation of the sheet 14 that may result in a change of the planar shape of the surface 16 of sheet 14. Such deformations are unwanted since a 2D projection of the sheet 14 or surface 16, as it results from taking an image of the template 10, which is the basis for determining any subject dimensions of a subject's face, would probably show different shapes of the markings 22, 24, 26 and/or 28 or show distances between those markings that do not correspond to the real distances on a flat surface 16 and therefore lead to wrong subject dimensions when using the markings as references. Therefore, in these embodiments folding lines 30, 32, 34 and 36 are indicated on the sheet 14. Along these folding lines 30, 32, 34 and 36 an outer rim 38 can be folded back- or outwards such that with respect to the representation of the FIG. 1 this rim 38 is moved back away from the viewer of the figure while the surface 16 of sheet 14 remains in the plane of the representation. This is indicated by instructions 39 on the sheet 14, for example stating "Fold outwards". A folding along at least some of those folding lines 30, 32, 34 and/or 36, preferably along all these folding lines, leads to a stabilized template 10, wherein the surface 16 of sheet 14 comprising the markings 22, 24, 26 and 28 as well as the opening 18 still remains in a shape with a planar surface 16. In other words, the planar shape of the surface 16 gets stabilized and unwanted deformations are prevented that way.

Figure 2:
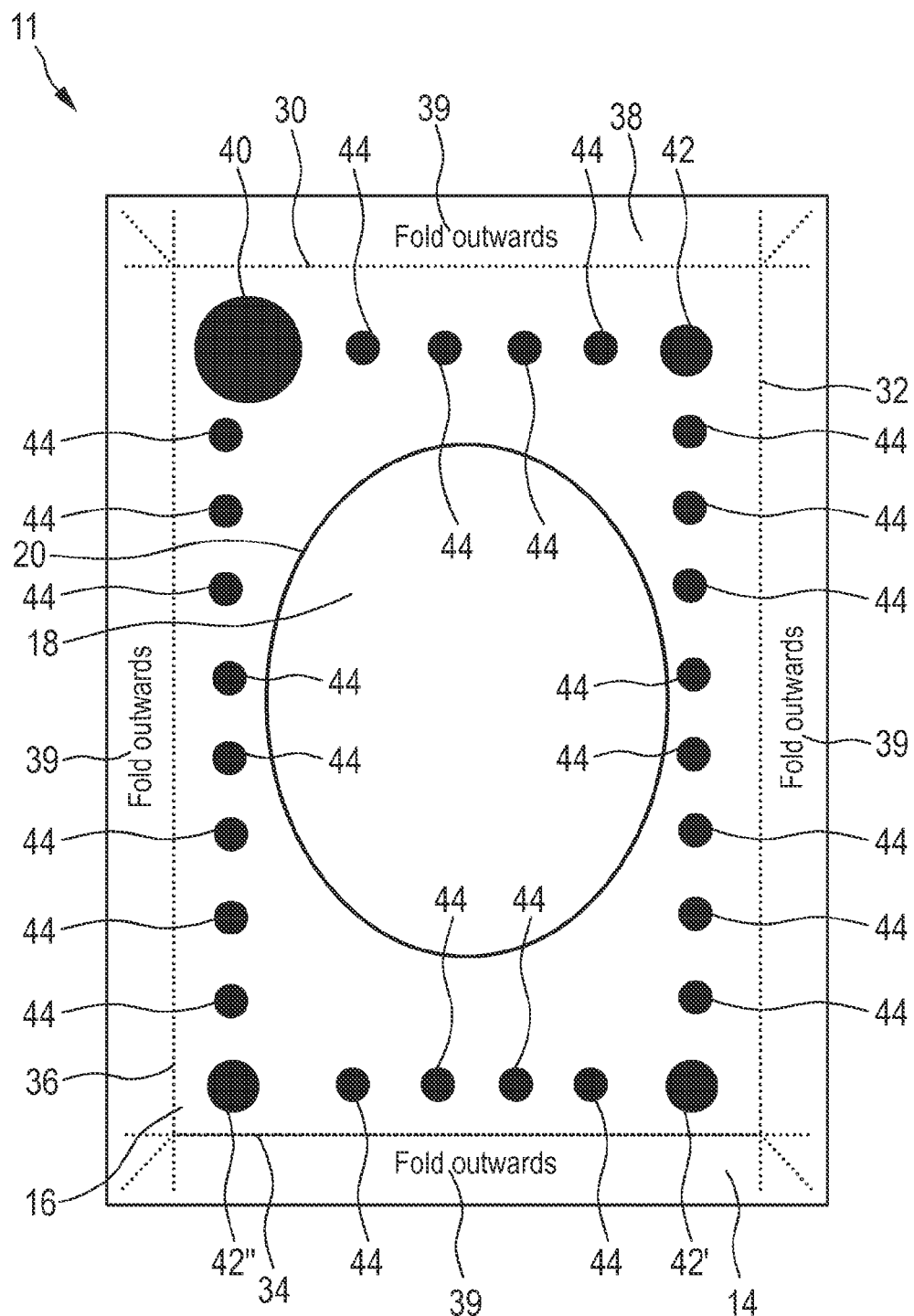
FIG. 2 shows a schematic view of a second template according to an embodiment of the present invention.

FIG. 2 shows the template 11 which basically corresponds to template 10 of FIG. 1 as described before. The primary difference between template 10 and template 11 lies in the markings used. In the following description and for the description of FIG. 2 in general, identical parts of the template 11 compared to template 10 are designated by the same reference numeral.

On the illustrated sheet 14 comprising the surface 16 of template 11, also an opening 18 for the face of the subject is provided. Surrounding the opening 18 cut markings 20 are provided as well. Further, around opening 18 on surface 16 several markings 40, 42 and 44 are arranged. In the present example of template 11, markings 40, 42 and 44 are designed as solid circles. In template 11, three different kinds of circles are provided for markings 40, 42 and 44. In the upper left corner with respect to the representation of FIG. 2, a relatively big circle can be found as marking 40. In contrast to this, smaller circles are used for the other remaining three corners of template 11, i.e. the markings 42, 42' and 42". In between those markings in the respective corners, meaning for example between marking 40 and marking 42, or marking 42 and marking 42', several even smaller circles are disposed as markings 44. The markings 44 in this template 11 are basically aligned on the horizontal and vertical connecting lines (with respect to the representation) between the respective markings 40, 42, 42' and 42" from one to the other corner. Those markings 40, 42, 44 represent another kind of fiducial markings.

The remaining parts of template 11, like for example the folding lines 30, 32, 34 and 36 or instructions 39, are identical to template 10 and are not described again in more detail.

Figure 3:
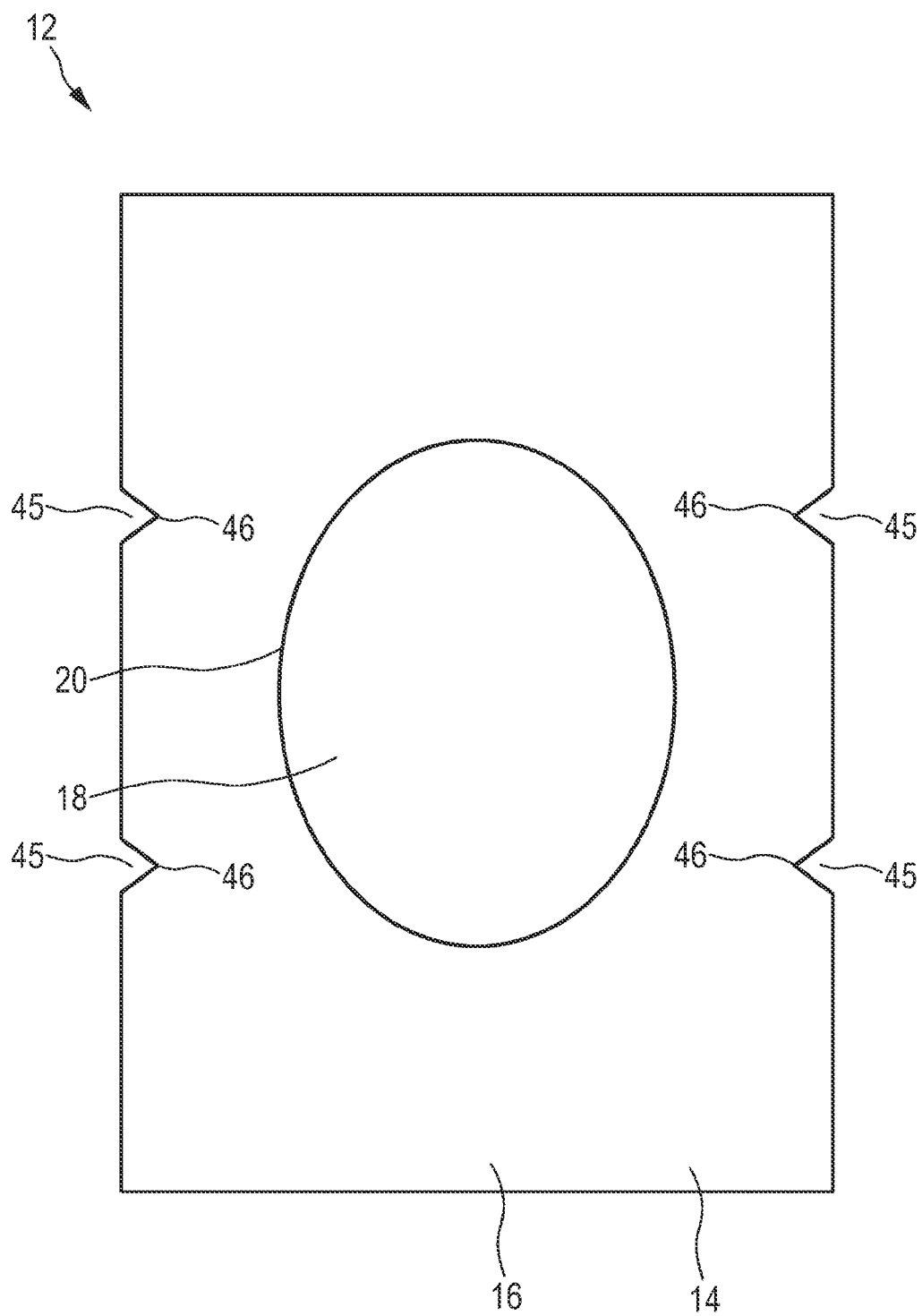
FIG. 3 shows a schematic view of a third template according to an embodiment of the present invention.

FIG. 3 shows another template 12. Therein, identical parts of the template 12 compared to templates 10 and 11 are designated by the same reference numerals. This template 12 also comprises a sheet 14 with surface 16. In surface 16, also an opening 18, surrounded by cut marking 20, is provided. In this regard, template 12 is identical to templates 10 and 11. However, template 12 comprises cut outs 45 on its longer sides, with respect to its rectangular shape and the representation of FIG. 3. These cut outs 45 comprise a triangular shape leading to a respective edge 46. Each of the edges 46 has a defined position on the surface 16 and therefore, exact dimensional information, i.e. distances between the edges 46, can be derived from those edges 46.

The edges 46 can therefore also be regarded as fiducial markers. In order for the edges 46 being easily detectable in an image of the template 12, a high contrast between the surface 16 and the background in the image is beneficial.

Figure 4:
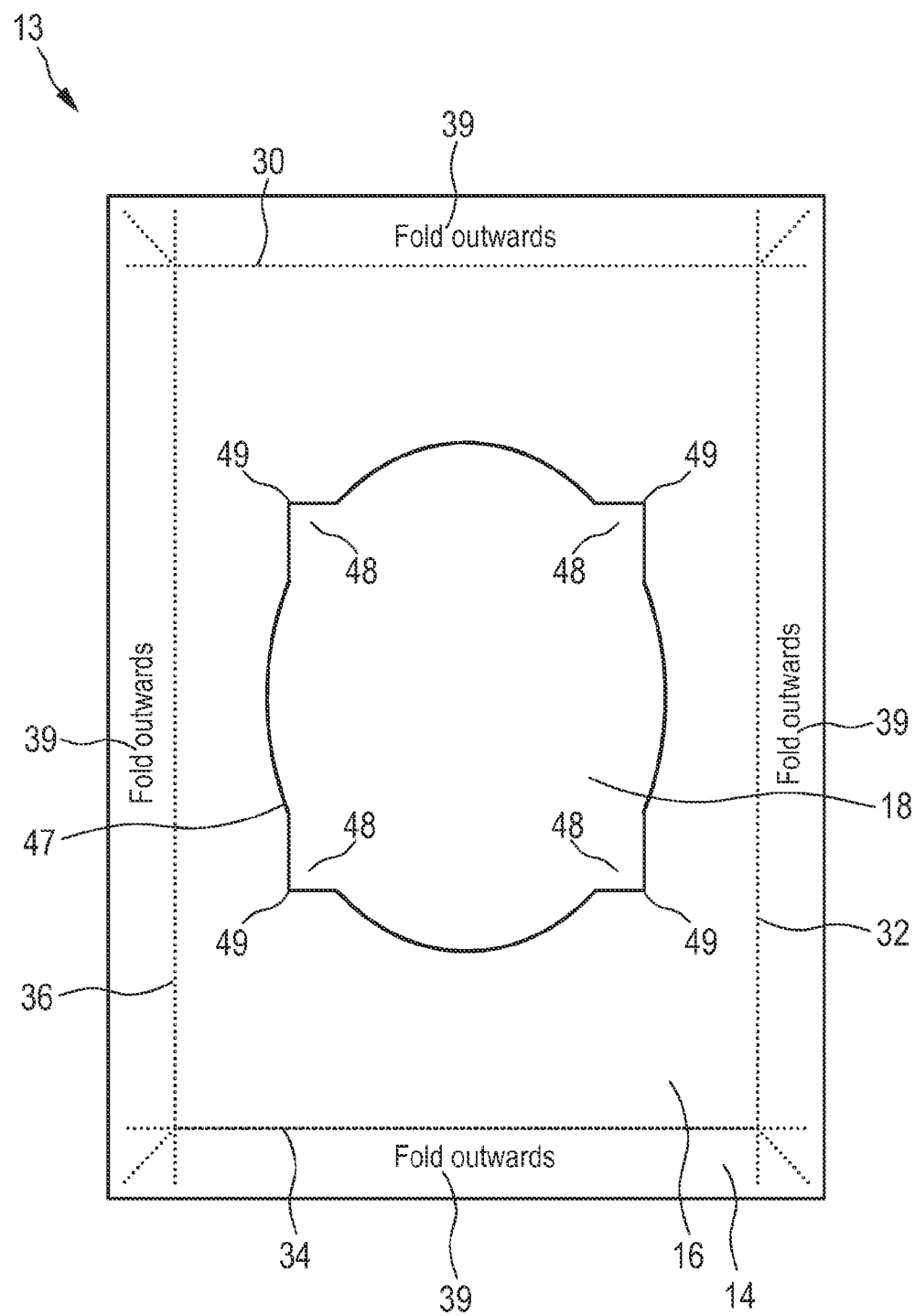
FIG. 4 shows a schematic view of a fourth template according to an embodiment of the present invention.

FIG. 4 shows a fourth embodiment of a template, i.e. template 13. Therein, identical parts of the template 13 compared to templates 10, 11 and 12 are designated by the same reference numerals. Having a sheet 14 with a surface 16 and an opening 18, template 13 is also similar to templates 10, 11 and 12. Analogue to templates 10 and 11, template 13 also comprises folding lines 30, 32, 34 and 36, as well as instructions 39.

In contrast to templates 10, 11 and 12, template 13 comprises a cut marking 47 surrounding opening 18. This cut marking 47 differs from cut marking 20 of the other template embodiments in that cut outs 48 are provided in the ellipse like shape of cut marking 20. These cut outs 48 comprise a triangular shape which results in edges 49. Those edges 49 are oriented such that they point in a direction away from the opening 18 of template 13. Similar to edges 46, edges 49 can be regarded as fiducial markers as well. Accordingly, a high contrast between the surface 16 and the background, in this embodiment in the opening 18, is beneficial for a reliable and exact detection of the edges 49 in an image of template 13, for example by a computer. Since the background is typically provided by a face of a subject in opening 18, such a contrast is advantageously generally given within this embodiment.

Although, three types of markings have been described before in the context of templates 10, 11, 12 and 13, it goes without saying that any suitable kind of a marking can be used on the surface 16 of the sheet 14 of a desired template that can be detected by a computer or computer-like device on the surface 16 such that further information from the marking or the markings that provide in the end the ratio between the distances and/or positions in the image to the subject distances and/or positions can be derived. Further, the respective marking should be suitable for achieving information about the viewing angle of a respective camera on the respective template such that parallax errors and wrong measurements can thereby be avoided or at least be recognized and taken into account in the following calculations of the computer or computer-like system when determining face dimensions as will be described later on.

Furthermore, the number of markings used can vary, as is already apparent from templates 10, 11, 12 and 13. Basically, the number of markings used should be suitable in order to be able to benefit from the advantages and features contributed by those markings. Further, it goes without saying that any suitable combination of the different markings of templates 10, 11, 12 and/or 13 may be used.

The manufacturing of the templates 10, 11, 12 or 13 can be done in different ways. As mentioned before, a sheet-like material, like the sheet 14 as a basis for the respective template 10, 11, 12, 13 is preferred within the present invention. This sheet-like material can in general be any thin metal, plastic, paper, cardboard or other suitable material that is preferably light weight and easy to produce. On this material, the respective markings and/or folding lines (if necessary) can be arranged via a suitable method like attaching separately, for example as an adhesive label, printing, or the like. Further, also a usage of a gauge-like back (not shown), preferably made of a material that is more stable and less prone to deformation, like cardboard, plastic, metal, can be used on which another thin sheet, like a foil or a paper, can be attached, for example by use of an adhesive. Therein this additional sheet comprises the desired markings for the purpose of the template 10, 11, 12 or 13. If such a stable material is used like in the last described embodiment with the stable back or in any other embodiment which uses a more stable material for the sheet 14, a folding and therefore the described folding lines 30, 32, 34 and 36 are not necessary. This gauge-like back may also comprise further elements that support the fit of the template 10, 11, 12, 13 on a subject or the subject's face.

In a preferred embodiment of the templates 10, 11, 12 and 13, the sheet 14 is realized by a sheet of paper. This paper and therefore the sheet 14 in general can be of any suitable size, that allows an opening 18 having a size such that it can accommodate the face of the subject and an additional surrounding surface 16 that leaves enough room for the markings to be arranged thereon. In a preferred embodiment of the present invention, the sheet 14 is a paper sheet made of standard printing paper, like in the sizes of DIN A4, US legal or US letter. Aside from those mentioned examples, any size smaller, equal or larger can be used as long as it fits the size of the template 10, 11, 12, 13.

This way, it is possible that the template 10, 11, 12 or 13 may even be distributed to a user in a digital format, like PDF, such that the user may then print out the template 10, 11, 12 or 13 on a regular printer using regular paper. Thereby, either a general standard file comprising the printable data for the respective template 10, 11, 12 or 13 may be used for each subject or also a subject specific file may be provided by the user, a manufacturer or a provider of the patient interfaces for every subject individually. In such a file, it would even be possible to include either markings that can be individualized, like the afore mentioned matrix-code like markers, that allow to identify the subject only by the image taken or also additional indicators, like barcodes or matrix codes. If the subject is the user, this way, the subject may take a photo/image at home and then send the image taken to a manufacturer or provider of the patient interfaces who then may identify the subject and derive the necessary dimensions for the patient interface only based on the information in the image according to the present invention.

In another embodiment, the user may use a program on a computer or a so called app on a smartphone or tablet PC that is able to determine the subject dimensions according to the present invention. This processed subject dimensions can then be either transmitted directly by the program or app, or manually by the user to the manufacturer or provider of the patient interfaces.

If the user prints out the template 10, 11 or 12 he/she may then cut out the opening 18 along the cut marking 20. For this, the representations in FIGS. 1 and 2 of templates 10, 11 and 12 can also be regarded as showing the respective template 10, 11, 12 before the cutting step. Therein, 18 would then depict the part that should be cut away. The same works for the cut outs 45 and 48 of templates 12 and 13 and the cut marking 47 of template 13. After that the user may use the folding lines 30, 32, 34 and 36 in order to fold back the rim 38 of the sheet 14 (in templates 10, 11 and 13). Thereby, a template 10, 11 or 13 results that is less prone to deformations which may normally occur due to the thin sheet material of the paper sheet 14.

Figure 5:
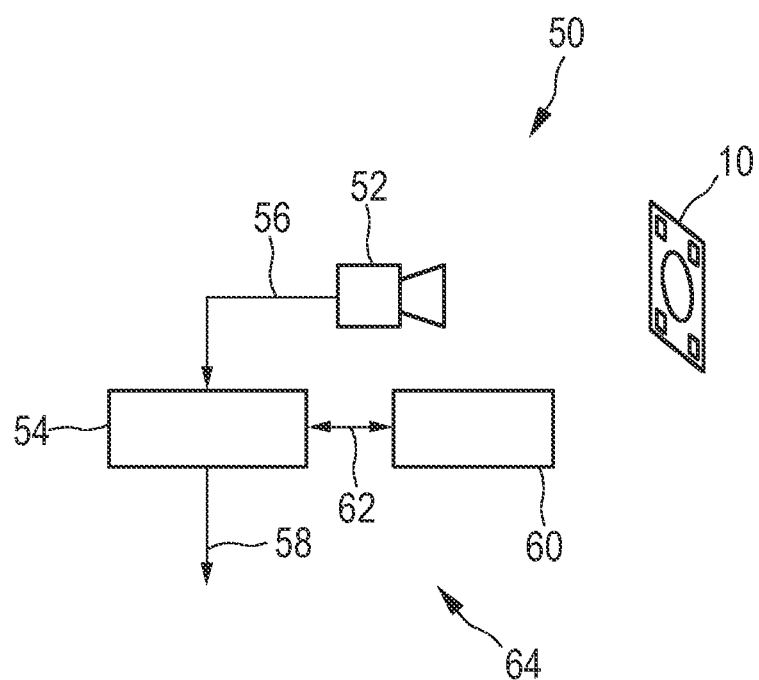
FIG. 5 shows a schematic view of a system according to an embodiment of the present invention.

The system 50 according to the present invention is shown and described within the context of FIG. 5. This system 50 comprises in this embodiment the template 10, which is schematically illustrated in FIG. 5. However, it goes without saying that any template suitable for the purpose of the present invention, like also the template 11, 12 or 13, may be used in a system 50 according to the present invention.

Further, system 50 comprises a camera 52. This camera may be any camera that can preferably record image data and submit those data electronically either via a direct connection or via a storage medium to another device. Camera 52 can therefore be any digital camera, web cam, computer integrated web cam, camera in a tablet PC or smartphone, or the like.

In the present embodiment of system 50, the camera 52 is connected to a processing unit 54. Via this connection, the camera 52 may submit the recorded image data to the processing unit 54 for further processing. This connection is indicated by an arrow 56. The processing unit 54 is then able to detect the template within the image data provided by camera 52, to identify the face of the subject within the opening 18 of the template 10 and to recognize the relevant facial landmarks in the face of the subject in order to determine the relevant dimensions of the subject's face. Therefore, the processing unit 54 recognizes also any markings according to the present invention, like the markings 22, 24, 26 and 28 on template 10. The whole method of collecting the data of a face of a subject, which can be for example done with the processing unit 54, will be described later on in more detail. The processing unit 54 may comprise a processor and at least one memory (not shown) for storing routines that are executable on the processor and which are preferably the basis for the steps carried out by the processing unit 54.

The processing unit 54 may further provide the collected data of the face of the subject, preferably the anthropometric data to another device or a user of the processing unit 54. This is indicated by an arrow 58. Also, the processing unit 54 may be able to store the data received from camera 52, the processed data or any other related data to a database 60. Furthermore, processing unit 54 may also compare the received data from camera 52 as well as the data processed by the processing unit 54, e.g. the subject facial dimensions, with comparable data in the database 60. These mentioned data exchanges between processing unit 54 and database 60 are indicated by the double arrow 62.

The system 50 comprising a camera 52 and processing unit 54 can be realized such that the camera 52 and processing unit 54 are contained in one device, like a computer with integrated camera, a tablet PC or a smartphone with a camera. Also, systems are possible according to the present invention wherein the camera 52 and processing unit 54 are designed as separate devices. Therein, the camera 52 and processing unit 54 exchange the data via a cable, wireless or a storage medium, for example, which correspond to arrow 56. This may for example be the case if the camera is a separate web camera connected to a computer, which corresponds to processing unit 54, or where the camera 52 is a web camera, a digital camera, or any other camera device, located at the user and the processing unit 54 is located at another location, like at the manufacturer or provider of the patient interfaces. In this exemplary set up the user merely takes the image of the subject and the template 10, 11, 12, 13 and sends these image data via a storage medium or the internet, for example, to the manufacturer or provider who will then process the data according to the present invention and corresponding to processing unit 54. In the case, where the subject is the user, he/she may take an image of himself/herself and proceed accordingly.

The processing unit 54 may also be a part of a computing device 64. This computing device 64 may further comprise the database 60 and/or the camera 52 or may at least be connected to at least one of them as indicated by arrows 56, 58 and 62. If the computing device 64 is connected to those devices, this may be done by input and output interfaces (indicated by the arrows 56, 58 and 62).

In the following and within the context of FIGS. 6 and 7, the usage of the template 10 and accordingly the method for collecting data of a face of a subject shall be described in more detail. It goes without saying that although template 10 is used for the following explanations, also templates 11, 12, 13 or any other suitable template may be used accordingly.

Figure 6:
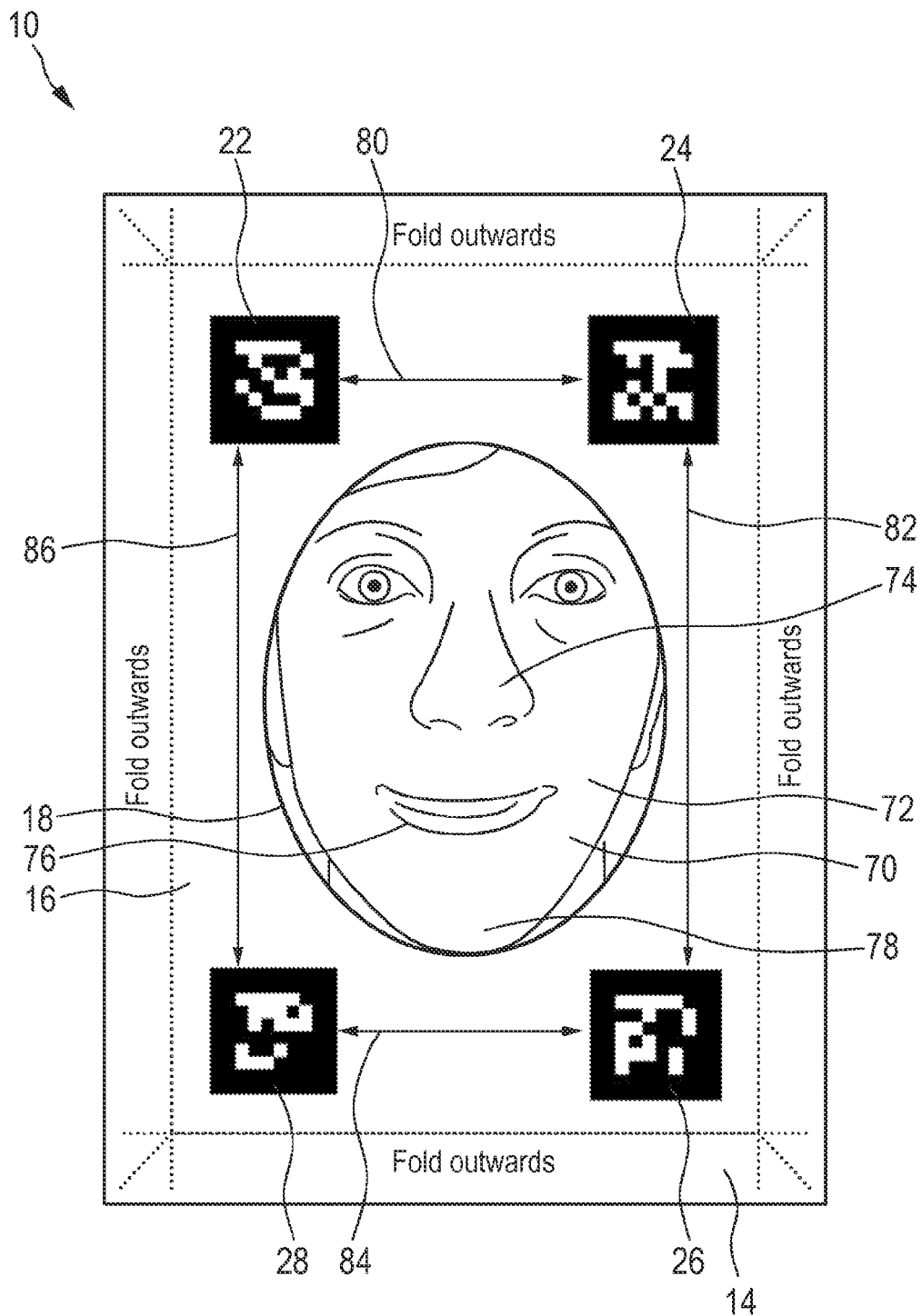
FIG. 6 shows a schematic view of the template of FIG. 1 used by a subject.

FIG. 6 shows the template 10 with the opening 18 in the surface 16 of sheet 14. Within this opening 18, a subject 70, especially his face 72, is positioned. The relevant subject dimensions shall be determined of this face 72 in order to equip the subject with a comfortable and a suitable patient interface, like a full face mask for example. Therefore, the most important facial dimensions such as the width and height of the nose 74, the width of the mouth 76 and the distance from the chin 78 to the upper end of nose 74 shall be determined. It goes without saying that the afore mentioned dimensions are merely mentioned by way of example and that it is not intended to limit the relevant dimensions to these three dimensions/distances. Actually, any suitable dimensions or distances that can be used for fitting patient interfaces to a face of the subject 70 may be determined by the method and with the system 50 and template 10, 11, 12, 13 according to the present invention.

When using the template 10, 11, 12, 13, a subject 70 may easily hold the template 10, 11, 12, 13 with his/her hand such that his/her face 72 lies within opening 18 of the respective template 10, 11, 12, 13. Thereby, all the relevant facial landmarks are located approximately in the same plane as the template 10, 11, 12, 13, meaning in the same plane as the surface 16. Aside from the way of arranging template 10, 11, 12, 13 by the subject 70 himself/herself as mentioned before, any other suitable way of arranging the template on the subject's face 72 is possible. For example, a user may hold the template on the face 72 of the subject 70 or a stand (not shown) or the like may be used.

After detecting the relevant facial landmarks, which will be explained within the context of FIG. 7 later on, the dimensions within the image of template 10 with subject 70 can be determined. In order to transform those dimensions in the image to subject dimensions that are present in reality, the dimensions and distances of the markings 22, 24, 26 and/or 28 may be used as mentioned before. Accordingly and by way of example, it is possible that the distance between marking 22 and marking 24, which is indicated by an arrow 80, is known. Correspondingly, the distances between markings 24 and 26, 26 and 28, and 28 and 22 may be known as well. These are indicated by arrows 82, 84 and 86, respectively. If the subject reference distances 80, 82, 84 and/or 86 are known, meaning on the real template 10 as for example printed out by the user, e.g. the subject 70, the corresponding distances 80, 82, 84 and/or 86 between the markings 22, 24, 26 and/or 28 within the image, taken by camera 52 for example, can be determined and put in relation to the subject reference distances as mentioned before. Thereby, a correlation or scale between the dimensions within the image of template 10 and subject 70 and the subject dimensions may be provided. Accordingly, the image dimensions within the face 72 of the subject 70 as mentioned before may be transformed to the subject dimensions of the face 72 of the subject 70.

Figure 7:
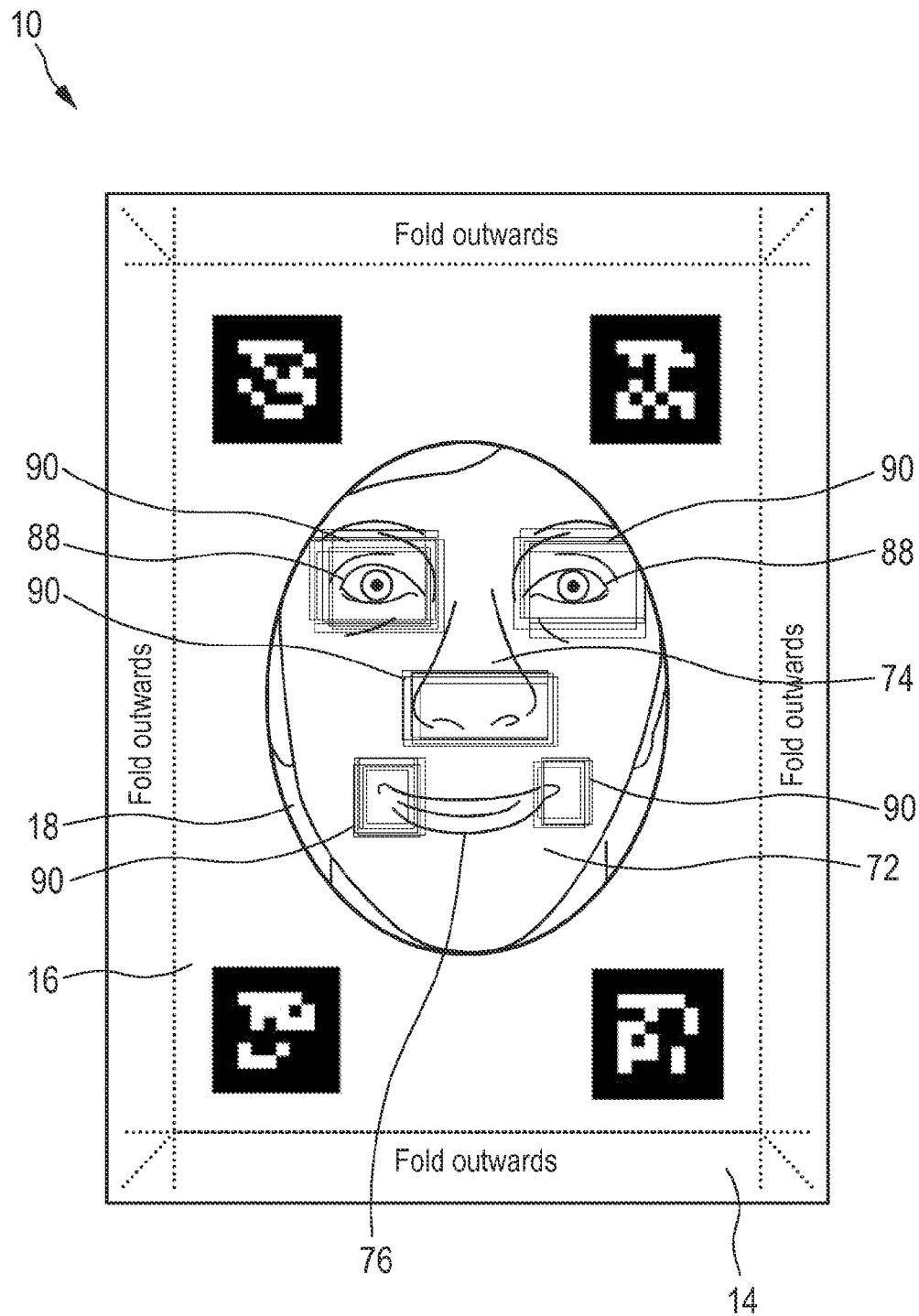
FIG. 7 shows the schematic view of FIG. 6 with additional rectangular markings of facial landmarks in the face of the subject.

In FIG. 7 a determination of the most relevant facial landmarks is exemplary shown. This can for example be done by the processing unit 54, e.g. as part of the computing device 64. Therein, the processing unit 54 may recognize facial landmarks like eyes 88, the nose 74 or the mouth 76 of the subject 70. Therefore, a first face detection step will be applied to the image of template 10 and face 72 of the subject 70. Such a face detection step may be realized by an image based feature detection algorithm, for example by a Viola-Jones algorithm known from Viola and Jones, "*Rapid Object Detection using a Boosted Cascade of Simple Features*", in Computer Vision and Pattern Recognition, 2001, which is herein fully incorporated by reference. It goes without saying that also any other or analog algorithm may be applied in this face detection step.

After the face detection follows preferably a landmark detection step. This landmark detection step comprises a detection of face features inside the region of interest. For this step, image face feature detection algorithms can be applied.

Figure 8:
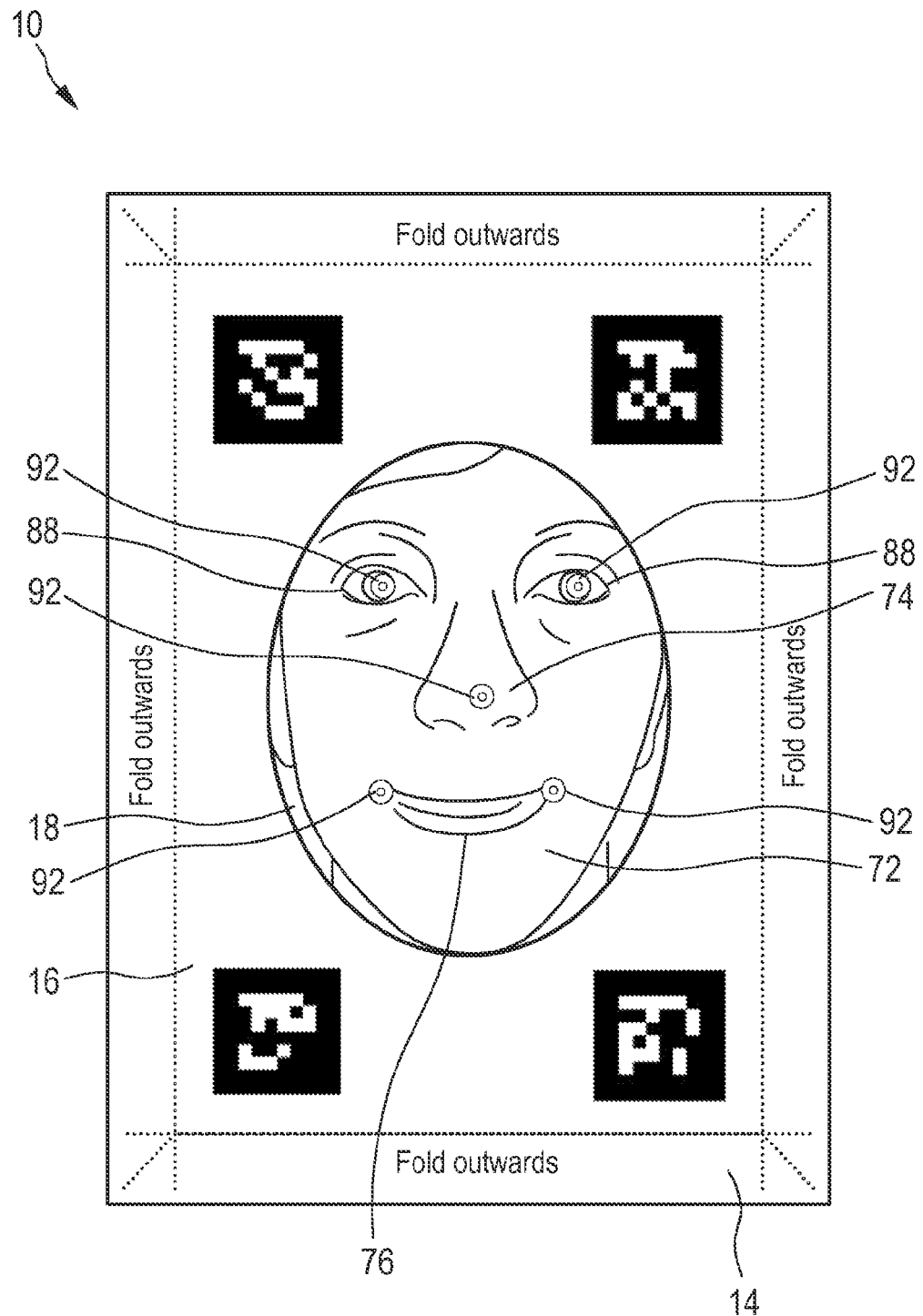
FIG. 8 shows the schematic view of FIG. 6 with additional circular markings of facial landmarks in the face of the subject.

FIG. 7 shows a typical result for a boosted cascade detection, based on Haar-like features, which are separately trained for detection of eyes, nose and mouth corners. The face detection algorithm returns a set of rectangles 90 around the probable face landmarks detected at different scale ratios. These rectangular positions are then averaged to determine a robust position of facial landmarks on the image of the template 10 and face 72. This is illustrated by FIG. 8 wherein big dots 92 refer to those located face landmarks. Based on these exemplary positions shown by the big dots 92, the afore mentioned facial dimensions can be determined in the image. These image based dimensions can then be transformed into subject dimensions by usage of the ratio or scale derived from the dimensions of the markings in the image and in reality as described before. Aside from the present embodiment, wherein the processing unit 54 is designed to process the steps of face detection and the detection and localization of the face features or facial landmarks, it is also possible that this information is provided to the system by the user. This may either be done alternatively or additionally, for example in the case that the processing unit 54 fails to identify the respective features. This can in an exemplary setup be realized by the user entering the positions of the respective facial landmarks in the image via an interface, like touching for each landmark the respective position on a touchscreen of a smartphone or tablet PC showing the image taken.

As a result, the user, like the subject 70, a medical professional or also the manufacturer or provider of the patient interfaces, gets these subject facial dimensions and can then decide which patient interface is suitable for a subject 70, for example is comfortable to wear and/or fits tightly and therefore without providing air leaks on the face 72 of subject 70. Also, these facial dimensions cannot only be used to choose a patient interface from a pool of patient interfaces but also to get exact data and dimensions for manufacturing or adapting a patient interface according to the actual facial dimensions of subject 70. This way, an optimal fit can be achieved for every subject 70 individually. Furthermore, aside from providing the facial dimensions to the user, the computing device 64, e.g. as part of the system 50, may also provide an advice which patient interface fits probably best to subject 70. Therefore, the processing unit 54 may compare the acquired and the determined facial dimensions with data stored in database 60 as mentioned before. Thereby a comparison with dimensions of patient interfaces or data based on experience with other comparable subjects can be done and an advice given, for example. This can be realized for example in two different ways. Either, the dimensions between the landmarks are used to find the closest fitting patient interface that was designed for those dimensions, or the positions of the landmarks are used to determine the minimal distances between them and a contour of the patient interface part that gets in contact with the patient's face in order to check for their deviation from optimal values, preferably choosing the patient interface that shows the smallest deviation. Also it would be possible, to let the computing device 64, e.g. as part of the system 50, control other devices that may produce or adapt a patient interface based on the determined data, i.e. with the subject facial dimensions of the subject. These productions or adaptations can be done by known methods, via computer-aided manufacturing (CAM), for example.

In the following, the method for collecting 3D data according to the present invention shall be briefly described within the context of FIGS. 9 and 10.

Therein, one can see a subject's face 72 within the opening 18 of a template 10 corresponding to the representation of FIG. 6. However, in FIG. 9 the image is taken from an angle that is deviating from a frontal orientation to subject 70 as shown in FIG. 6 slightly to the right from the point of view of subject 70. In FIG. 10, a further image is taken, wherein the deviation is to the left from the point of view of subject 70.

Due to the known markings 22, 24, 26 and 28, meaning not only the known distances or dimensions but also the known normal shape of those markings, it is possible for a computer or computer-like device, like for example the processing unit 54, e.g. as part of the computing device 64, to determine distance and orientation of subject 70 and template 10 with respect to the camera. This may for example be based on the change from an originally rectangular shaped to a non-rectangular shaped parallelogram or on the change from a circle to an ellipse in the two dimensional projection as a result of the image being taken from a non-orthogonal angle with respect to the template 10, 11, 12, 13. Thereby, these present rectangular or circular shapes may either result from the markings 22, 24, 26, 28, 40, 42 or 44 in templates 10 and 11 themselves, or from the rectangular shape indicated by the edges 46 or 49 in templates 12 and 13, wherein each edge 46 or 49 forms one edge of the rectangle, for example. The mentioned distances with respect to the camera can be determined via the dimensions in the image determined as mentioned before and the known specifications of the camera, for example.

Figure 9:
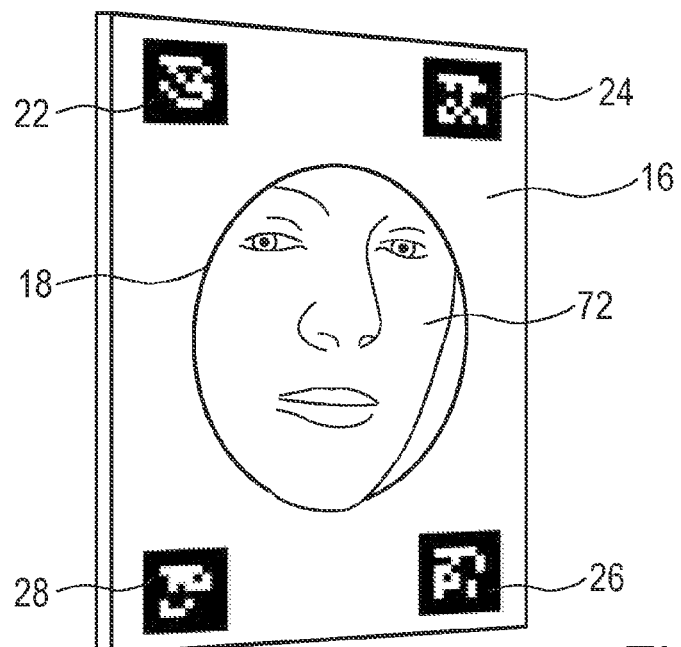
FIG. 9 and FIG. 10 show a respective schematic perspective side view of the representation of FIG. 6 from two different angles.
Figure 10:
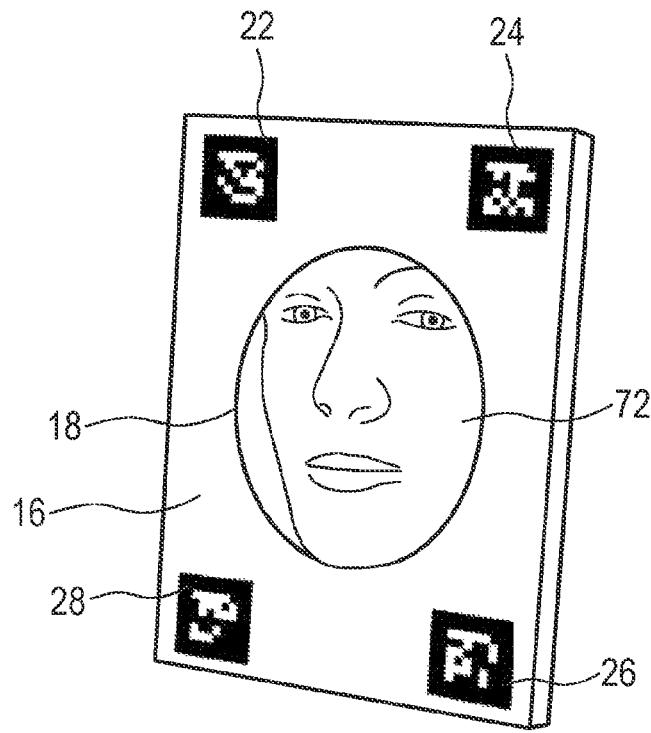

If this is done from at least two, preferably more and more preferably from three directions, like for example shown in FIGS. 9 and 10, the 2D projections of the face 72 of the subject 70 in the respective images, each with a different orientation, can be used to generate 3D data. In other words, the 3D shape of the face 72 of the subject 70 can be reconstructed from this 2D information. This works according to the method of the present invention using the template 10, 11, 12 or 13, by taking several single 2D pictures/images, for example with camera 52. This is possible by the template 10, 11, 12, 13 which serves as a reliable reference in order to determine distance and orientation of the object, i.e. subject 70, with respect to the camera. Using three directions gives a good compromise between preventing occluded face surfaces and using as few images as possible. Such a generation of 3D data can be realized by any method known for this purpose, for example by the methods described in Peter-André Redert, "*Multi-viewpoint systems for 3-D visual communication*", PhD thesis, University of Delft, 2000, ISBN 90-901-3985-0, which is herein fully incorporated by reference.

The thereby constructed 3D data of the face 72 of the subject 70 can then be used as well in steps analog to those as described before within the context of the FIGS. 6 to 8. Thereby, the relevant facial landmarks can be determined in the 3D model of the face 72 of the subject 70. Also a scaling of the whole 3D model to subject dimensions would be possible based on the markings as reference(s). This way, also a fitting of the mask virtually, meaning on a computer or computer-like device can be realized. Thereby, either an exact advice which patient interface is suitable for the subject 70 or even a manufacturing or adaptation of such a patient interface to subject 70 is possible and can be highly automated.

All the steps mentioned before that can be carried out by the processing unit 54 can be realized by a computer program that runs or is carried out on a computing device 64 with a processing unit 54, or a computer as/with a processing unit 54 in general.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality. A single element or other unit may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium supplied together with or as part of other hardware, but may also be distributed in other forms, such as via the Internet or other wired or wireless telecommunication systems.

Any reference signs in the claims should not be construed as limiting the scope.

The invention claimed is:

1. A computing device configured to provide subject facial dimensions of a subject based on at least two 2D images taken by a camera, wherein each of the 2D images shows the face of the subject and at least one computer-detectable element disposed on a template, and wherein the 2D images show the subject and the at least one computer-detectable element from different viewing angles, the computing device comprising:
   at least one output interface for providing the subject facial dimensions,
   at least one input interface for receiving the plurality of 2D images, and
   a processing unit including a processor and a memory, the memory storing one or more routines executable by the processor, the one or more routines being adapted to:
   process the 2D images,
   determine a reference distance between two of the computer-detectable elements on the template,
   determine a distance and orientation of the face and the at least one computer-detectable element relative to the camera in each of the 2D images based on at least one of a known dimension of the computer-detectable element and the reference distance between two of the computer-detectable elements,
   construct 3D data based on the 2D images and the determined distance and orientation of the face and the computer-detectable element relative to the camera in each of the 2D images, and
   provide subject dimensional data of the face of the subject based on the 3D data, and wherein the computer-detectable element is a marker.

2. The computing device of claim 1, wherein the computing device further comprises the camera.

3. The method of providing a patient interface for a subject, including the steps of:
   receiving 3D data of a face of the subject obtained by the computing device according to claim 2, and
   using the received 3D data of the face of the subject for manufacturing the patient interface for the subject, determining the shape of the patient interface for the subject and selecting a patient interface suitable for the subject from a predetermined set of patient interfaces.

4. The computing device of claim 1, wherein the one or more routines are further adapted to:
   determine facial landmarks within the 3D data of the face,
   determine a second reference distance based on the at least one computer-detectable element in the 3D data, determine facial dimensions based on the facial landmarks in the 3D data, and scale image dimensions in the 3D data to subject dimensions based on a ratio of the a second reference distance in the 3D data to a corresponding known subject reference distance based on the at least one computer-detectable element.

5. The computing device of claim 4, wherein the one or more routines are further adapted to generate based on the determined facial dimensions an advice for the subject, wherein the advice includes a patient interface that is suitable for the subject.

6. The computing device of claim 1, wherein the one or more routines are adapted to determine the distance and orientation of the face and the at least one computer-detectable element relative to the camera in each of the 2D images based on the known dimension of the at least one computer-detectable element and the known distance between two of said at least one computer-detectable elements.

7. The computing device of claim 1, wherein the one or more routines are adapted to determine the distance and orientation of the face and the at least one computer-detectable element relative to the camera in each of the 2D images based on the known dimension of the at least one computer-detectable element.

8. The computing device of claim 1, wherein the one or more routines are adapted to determine the distance and orientation of the face and the at least one computer-detectable element relative to the camera in each of the 2D images based on the known distance between two of said at least one computer-detectable elements.

9. A System for collecting data of a face of a subject, with a template for collecting data of the face of the subject, the template having a surface, an opening for the face of the subject in the surface and a plurality of computer-detectable elements for providing dimensional reference information, the system comprising:

a camera for recording a plurality of 2D images of the template and the face of the subject within the opening of the template, and a computing device configured to provide subject facial dimensions of a subject based on at least two 2D images taken by the camera, wherein each of the 2D images shows the face of the subject and at least one computer-detectable element, and wherein the 2D images show the subject and the at least one computer-detectable element from different viewing angles, the computing device comprising:

at least one output interface for providing the subject facial dimensions, at least one input interface for receiving the plurality of 2D images, and a processing unit including a processor and a memory, the memory storing one or more routines executable by the processor, the one or more routines being adapted to:

process the 2D images, determine a reference distance between two of the computer-detectable elements, determine a distance and orientation of the face and the at least one computer-detectable element relative to the camera in each of the 2D images based on at least one of a known dimension of the computer-detectable element and the reference distance between two of the computer-detectable elements, construct 3D data based on the 2D images and the determined distance and orientation of the face and the computer-detectable element relative to the camera in each of the 2D images, and provide subject dimensional data of the face of the subject based on the 3D data, and wherein the computer-detectable element is a marker.

10. The system of claim 9, wherein the camera is designed to send the image data to the computing device, and wherein the computing device is designed to receive the image data from the camera via the at least one input interface.

11. The system of claim 10, wherein the camera and the computing device are combined in one device.

12. The system of claim 9, wherein the template is manufactured of a sheet-like material.

13. The system of claim 9, wherein the template is made of a sheet of paper.

14. The system of claim 9, wherein the one or more routines are adapted to determine the distance and orientation of the face and the at least one computer-detectable element relative to the camera in each of the 2D images based on the known dimension of the at least one computer-detectable element and the known distance between two of said at least one computer-detectable elements.

15. The system of claim 9, wherein the one or more routines are adapted to determine the distance and orientation of the face and the at least one computer-detectable element relative to the camera in each of the 2D images based on the known dimension of the at least one computer-detectable element.

16. The system of claim 9, wherein the one or more routines are adapted to determine the distance and orientation of the face and the at least one computer-detectable element relative to the camera in each of the 2D images based on the known distance between two of said at least one computer-detectable elements.

17. A method for collecting 3D data of a face of a subject, comprising the following steps:

providing at least two 2D images taken by a camera, wherein each of the 2D images shows the face of the subject and at least one computer-detectable element, and wherein the 2D images show the subject and the at least one computer-detectable element from different viewing angles;

determine a reference distance between two of the computer-detectable elements provided on a template;

determining a distance and orientation of the face and the at least one computer-detectable element relative to the camera in each of the 2D images based on at least one of a known dimension of the at least one computer-detectable element and the reference distance between two the computer-detectable elements, and constructing 3D data based on the 2D images and the determined distance and orientation of the face and the computer-detectable element relative to the camera in each of the 2D images, and wherein the computer-detectable element is a marker.

18. The method of claim 17, further comprising the following steps:

providing facial landmarks in the 3D data of the face, determining a second reference distance based on the at least one computer-detectable element in the 3D data, determining facial dimensions based on the facial landmarks in the 3D data, and scaling image dimensions in the 3D data to subject dimensions based on a ratio of the second reference distance to a corresponding known subject reference distance based on the at least one computer-detectable element.

19. A computer program stored on a non-transitory computer-readable medium comprising program code means for causing a computer to carry out the steps of the method as claimed in claim 17 when said computer program is carried out on a computer.

20. The method of claim 17, wherein the determining comprises determining the distance and orientation of the face and the at least one computer-detectable element relative to the camera in each of the 2D images based on the known dimension of the at least one computer-detectable element and the known distance between two of said at least one computer-detectable elements.

21. The method of claim 17, wherein the determining comprises determining the distance and orientation of the face and the at least one computer-detectable element relative to the camera in each of the 2D images based on the known dimension of the at least one computer-detectable element.

22. The method of claim 17, wherein the determining comprises determining the distance and orientation of the face and the at least one computer-detectable element relative to the camera in each of the 2D images based on the known distance between two of said at least one computer-detectable elements.

* * * * *